(12) United States Patent
Wildi et al.

(10) Patent No.: US 6,794,183 B2
(45) Date of Patent: Sep. 21, 2004

(54) DEVICE FOR CULTIVATING PLANT OR ANIMAL TISSUE CULTURES

(75) Inventors: Eckhart Wildi, Eschelbronn (DE); Reinhart Wildi, Binningen (CH); Peter Ripplinger, Neckargemuend (DE)

(73) Assignee: Rootec Gesellschaft Für Bioaktive Wirkstoffe mbH, Heidelberg (DE)

(*) Notice: Subject to any disclaimer, the term of this patent is extended or adjusted under 35 U.S.C. 154(b) by 0 days.

(21) Appl. No.: 10/240,596

(22) PCT Filed: Apr. 2, 2001

(86) PCT No.: PCT/EP01/03716
§ 371 (c)(1),
(2), (4) Date: Dec. 30, 2002

(87) PCT Pub. No.: WO01/74992
PCT Pub. Date: Oct. 11, 2001

(65) Prior Publication Data
US 2003/0129743 A1 Jul. 10, 2003

(30) Foreign Application Priority Data
Apr. 3, 2000 (DE) .......................................... 100 16 554

(51) Int. Cl.⁷ ................................................. C12M 1/00
(52) U.S. Cl. ................................ 435/289.1; 435/296.1; 435/299.1; 435/299.2
(58) Field of Search .......................... 435/289.1, 296.1, 435/299.1, 299.2

(56) References Cited

U.S. PATENT DOCUMENTS

| | | | |
|---|---|---|---|
| 5,350,080 A | 9/1994 | Brown et al. | |
| 5,585,266 A | 12/1996 | Plitt et al. | |
| 6,107,085 A | * 8/2000 | Coughlin et al. | ........ 435/299.1 |

FOREIGN PATENT DOCUMENTS

| | | |
|---|---|---|
| CH | 372 911 A | 10/1963 |
| DE | 1 611 044 | 9/1970 |
| EP | 0 234 868 B1 | 6/1992 |
| FR | 2 786 783 A1 | 6/2000 |
| GB | 2 202 549 A | 9/1988 |
| WO | WO 89/10958 A2 | 11/1989 |
| WO | WO 96/36703 A1 | 11/1996 |

* cited by examiner

Primary Examiner—David A. Redding
(74) Attorney, Agent, or Firm—Foley & Lardner LLP (57) ABSTRACT

The present invention relates to a device for cultivating plant or animal tissue. The inventive device comprises a fermenter container, a supply device for liquid nutrients and gases, devices for discharging used nutritive liquids and gases and solid carrier plates for the plant tissues which are permeable to said liquid nutrients and gases and are arranged within the fermenter container in a stationary manner. According to the invention, the fermenter container comprises a dimensionally stable lid component that carries the various supply and discharge lines as well as the carrier for the cells and comprises a pot- or bag-shaped plastic hose. The opening of said hose is sealed against the lid and is fixed.

16 Claims, 5 Drawing Sheets

DEVICE FOR CULTIVATING PLANT OR ANIMAL TISSUE CULTURES

The subject of the present invention is a new device for the culturing of plant or animal tissue or organism cultures (in the following called tissues), as well as culturing processes with the use of such devices.

BACKGROUND OF THE INVENTION

The culturing of cells for the production of cell material and especially of metabolic products of these cells is of continuous importance since the chemical synthesis of such products is frequently difficult or impossible or proves to be uneconomical in comparison with the biochemical production. Besides the already long known culturing to a wide extent of yeasts, moulds and bacteria, the culturing of plant and animal cells is also to an increasing extent of importance for the production of certain products. The investigation of suitable culturing conditions and possibly the genetic change and culturing of plant and animal cells occurring in nature for the achievement of high yields are thereby urgent objectives of research.

One differentiates plant or animal cell and tissue cultures (preferably cell suspensions, callus cultures) from plant organ cultures (transformed root hair (hairy root), root or shoot cultures (shooty teratomas)). For the fermentation, hitherto there were used, above all, cell suspension cultures which consist of undifferentiated individual cells or cell aggregates. Since the 1980's, intensive efforts have been underway to culture these cell suspension cultures in large scale fermenters and to use them for the commercial production of tissue component materials.

However, apart from a few exceptions, it has been shown that cell suspension cultures are genetically frequently unstable (somaclonal variation). This has a serious influence on the active material production since even promising high capacity cell lines can, after a few cycles, be subject to great variations or the production of the active materials is completely suppressed. One has attributed this instability to the influence of growth regulators, as well as to the undifferentiated state of the cells which are frequently revealed as not stable without sufficient differentiation of cell organelles or without corresponding cell-cell contact of individual biosynthesis routes. Thus, epigenetic factors play a quite important influence for the biosynthesis.

Plant organ cultures and here, above all, the commercially interesting transfonned root hair cultures form differentiated tissues which also in long-term cultures prove to be genetically clearly more stable than cell suspension cultures. Thanks to the rapid growth of transformed root hair cultures, which frequently display comparable growth rates to cell suspension cultures, these organ cultures are suitable for the fermentative production of commercially interesting component materials. Above all, transformed root hair cultures—other than cell suspension cultures—can be cultured without growth regulators. By way of example, reference is made to the synthesis of taxoids, podophyllotoxins or rosmaric acids which are produced by such processes. Individual growth regulators can inhibit the biosynthesis of secondary metabolites.

However, plant and animal organ cultures require a completely new fermenter design since a scale-up of the laboratory fermenter installations makes difficult the gas and nutrient solution provision due to the inhomogeneous tissues which cannot be mixed up.

For the culturing of tissues, it is necessary regularly to supply to the cells with mineral materials, growth regulators, carbon sources, normally saccharose, fructose or glucose, as well as possibly gases, such as oxygen or carbon dioxide, necessary for the nutrition of the cells.

The simplest and most economic form of the culturing of cells is the suspension culture, whereby isolated cells are suspended in a nutrient liquid, consumed nutrient components are regularly supplied to the nutrient solution and possibly a gassing is carried out for the maintenance of the suspension and nutrition of the cells. By means of appropriate growth regulators, a growing together of the cells to give comparatively large aggregates is prevented. It thereby proves to be disadvantageous that many plant or animal cells are not viable for a long time in this form and the formation of metabolites which are difficult to eliminate from the culture liquid requires a frequent transfer of the cells into fresh nutrient solution.

For smaller cultures, it is possible to inoculate the cells on to the surface of nutrient-containing gels, for example on to Petri dishes containing agar, whereby the cells take up the necessary nutrient components from the gel and the surrounding atmosphere. In the case of this method, too, it proves to be disadvantageous that under these conditions, many cells grow poorly and only slowly and metabolites separate out which, in part, enrich in the surrounding medium and again slow down the growth of the cells and the cell division or even kill off the cells. By means of the fixing on the gel surfaces, the cells grow to comparatively large heaps which, in turn, has the disadvantage that only the surface is in contact with the gas and the lower side with the nutrient liquid and thus slows down the nutrient supply in the case of growth. Here, too, in order to maintain a sufficient growth, a frequent inoculating over of the cultures to new nutrient bases is necessary.

In order to avoid the suspension culture of isolated cells, one has, therefore, changed over to culturing differentiated cultures, such as "hairy roots" or plant shoots or leaf tissue. In suspension, such comparatively large aggregates tend to dehomogenisation, especially in comparatively large reactors, whereby a change or adaptation of the process conditions was necessary by means of which a uniform supplying of the cell aggregates with nutrient solution and the necessary gases is achieved.

A widely used process is based on the fixing of the tissues to solid carriers and allowing a thin layer of nutrient liquid to run over the carrier so that the tissues are continuously supplied with fresh nutrient solution and, at the same time, possess a sufficient contact to the gas atmosphere in the reactor. As carrier bodies there are used plates or fabrics, especially mesh grids or rod constructions, as substrate which are arranged at a distance parallel to one another in appropriate reactors so that the intermediate spaces make possible an impingement with nutrient liquid and gas and a certain growth of the cell culture. The fixing of the cells on the carrier thereby takes place e.g. by squeezing into the gaps or angles of the carrier surface (cf. EP 234 868 and U.S. Pat No. 5,585,266). For the fermentation of so-called "hairy root cultures", the use of fermenters which contain a system of taut wires is especially recommended, whereby the distance of the wires at the crossing points is so small that the plant tissue is firmly held at these points or, by special formation of the wires with spikes, are firmly held in these spike axes (cf. WO 85/10958).

The fermentation vessels of the prior art usually consist, for reasons of stability, of metal, for example steel or aluminum sheet, or, because of transparency, of glass or acrylic glass and preponderantly have a cubic shape which makes possible a space-saving arrangement of several parallel carrier plate systems in the interior. A removable lid to which, possibly besides the inlet pipes, are also fixed the carrier plates, permits an access to the container, especially for harvesting of the cell culture and for cleaning. The production of the fermentation vessels from stable materials permits such reactors to be arranged fixedly next to one another on the bottom but has the disadvantage that the production and servicing of such vessels is expensive and does not permit an adaptation to the size of the culture.

Therefore, the task exists to find simple and economic devices for the culturing of tissues, especially of plant tissues, which are simple and economic to produce, are alterable in size and permit a simple handling and servicing.

In particular, it is an objective of the present invention, with the use of such fermentation devices, to make available a process for the culturing of plant tissue of the "hairy root type" or "plant shoot type".

BRIEF SUMMARY OF THE INVENTION

The present invention provides a device for the culturing of plant and animal tissue, comprising a fermenter vessel, an inlet for liquid nutrients and gases, as well as devices for removal of spent nutrient liquids and gases and solid carrier plates for the tissue which are permeable for the said liquid nutrients and gases and are fixedly arranged within the fermenter vessel, whereby the fermenter vessel comprises a form-stable lid part which carries the various inlet and outlet pipes as well as the carrier plates for the tissue and comprises a cup- or bag-shaped plastic tube, the opening of which is sealed off and fixed against the lid.

According to one embodiment 3–8 carrier plates are radially fixed on a central holding means and the supply of the nutrient solution takes place via 3–8 supply pipes present in the outer region between the plates.

According to a further embodiment the supply pipes contain bores as nozzles for the outlet of the nutrient solution and gas inlet pipes are guided parallel to the pipes which, in appropriate places, also contain bores from which gas emerges.

It is preferred that in the outer region between the carrier plates are arranged one or more sucking-off pipes for spent nutrient liquid and spent gas which on the end contain a sucking-off nozzle.

In another embodiment the inlet pipe represents a central pipe which comprises two or more tube pieces combined via intermediate adapters, whereby the adapter contains nozzles for the atomization of the nutrient solution and the tube pieces carry 3–8 radially projecting lattice plates as carrier plates for the cells, whereby the length of the assembled supply pipe corresponds to the length of the plastic tube of the fermenter vessel and the cross-section through the carrier lattice corresponds to the opening of the plastic tube or to the size of the lid.

It is preferred that, in the outer region between the carrier plates, one or more sucking-off pipes for spent nutrient liquid and spent gases are arranged which also comprises tube pieces which correspond in length to the tube pieces of the supply pipe and contain adapter pieces for the connecting of the tube pieces, as well as a sucking-off nozzle on the end, whereby the length of this pipe corresponds to the length of the plastic tube.

The carrier plates are arranged transversely to the longitudinal axis of the reactor or/and can be adjusted on a central holding means via tilt devices at an angle of 0–90° to the holding means.

In a further embodiment one or more devices are connected via appropriate pipe connections and holding devices to a central supply system. It is preferred that the nutrient solution is circulated via a nutrient solution tank in the form of a plastic sack.

DETAILED DESCRIPTION OF THE INVENTION

Surprisingly, it was possible to replace the rigid walls of the fermentation devices of the prior art by cup- or bag-shaped plastic tubes of thin synthetic resin foil when one fixes these via simple known connection devices, especially by squeeze connections, directly to the lid of a conventional fermentation vessel carrying inlet and outlet pipes for the nutrient agent and gas which carries the carrier plates for the fixing of the cells to be cultured.

Holding devices fixed over the lid enable such devices to be hung without problems in groups in appropriate stands, whereby these hanging stands simultaneously also carry the inlet and outlet pipes for the nutrient solutions and gases which can be regulated in their composition by central supply and control units. By means of a modular system of the inlet and removal pipes within the fermentation device of short pipe pieces with intermediately placed connection pieces and an arrangement of the carrier plates on these pipe sections, fermenters alterable in the length and thus in the capacity can easily be constructed and provided with tube foils of appropriate length as external wall so that it is possible to change the capacity of such a fermenter in definite steps. Usually, the tube foil is connected below with an inserted plastic bottom or by squeezing together and welding but it is also possible to insert a bottom piece, corresponding in diameter to the lid, of solid work material with an appropriate squeezing seal in which can possibly be fixed further inlet and removal pipes. Furthermore, the production of the fermentation container from light-permeable plastic foil permits the reactions taking place in the interior to be observed from the outside, as well as to introduce through the wall light or heat radiation which are needed especially for plant tissue culturing. It represents an especial advantage that for the removal of the cultured tissue for the production of subcultures or the working up of possible cell component materials, the outer plastic tubes can be cut up or, after loosening of the squeeze connection of the lid, without loosening of the inlet pipes to the lid with the carrier plates fixed thereon, can be pulled up possibly under a sterile laminar protective gas stream so that the culture carrier plate lies free and is available for a simple working up. The cleaning of the container necessary in the case of conventional containers of solid material does not apply since the plastic tubes are discarded after use and are replaced by new ones of suitable size.

The plastic tubes can consist of all commercially usual foils, polyethylene, polypropylene, polyvinyl chloride or polyester foils are especially preferred since they are not only especially economic to produce but also correspond in their chemical stability, elasticity, light permeability and strength to all necessary requirements. In the case of the choice of the plastic foil, only care has to be taken that these contain no plasticisers or other adjuvants from the production which can possibly act as poisons for the fermentation when they are dissolved out from the foil by the nutrient solution.

As carriers for the tissue to be cultured, there preferably serve grids or parallel-arranged rods of biologically inert materials, e.g. stainless steel, synthetic resins or a textile fabric stretched in a frame which, as radial plates, project from the central supply pipe of the nutrient solution, whereby this supplying preferably consists of several short tube pieces to which are fixed the correspondingly wide plates and the tube pieces are connected by intermediate pieces which serve as outlet nozzles for the nutrient liquid so that nutrient liquid can be sprayed at regular intervals into the fermentation container and thus bring about a uniform moistening of the culture surfaces from the middle. Alternatively, however, a dosing in of the nutrient solution can also take place via separate supply pipes in the outer region between the radial plates, whereby the central pipe then only functions as carrier of the plates.

By fixing of correspondingly dimensioned lattices of steel wire or synthetic material in a firm outer frame, which preferably consists of stainless steel, the carrier system, on the one hand, can be adapted to the plant tissue to be cultivated in the size and formation of the contact places (crossover points), on the other hand, taken apart for the harvesting of the cell tissue and for cleaning.

Alternatively to a radial arrangement, it is possible also to arrange the plates transversely to the direction of the central guide whereby a 0–90° angle between plate and guide permits the rate of flow-off of the nutrient liquid over the plate to be influenced which is the higher the steeper the plate stands in the reactor. Preferably, therefore, this angle can be adjusted via appropriate tilting devices, for example hinges. Positioning and cleaning of the device is also simplified by this tilting possibility.

The production of the nutrient liquid in the form of fine mist droplets is per se known (EP 0 234 868 B1) and has proved to be especially useful for the nutrient supply for the plant cells since, at the same time, a high gas exchange is brought about. Excess or spent nutrient solution can, on the basis of gravity, drop off from the plates to the bottom of the vessel from where, by an appropriate sucking off device, the liquid can, after regeneration, i.e. the provision of consumed nutrients and the separating off of the metabolites formed, be returned into the fermenter. The sucking off pipes are also provided with appropriate modular units, whereby the intermediate pieces are naturally not formed as nozzles but rather as continuous connections in order, in this respect, to make possible a change of size of the fermenter.

The supplying of the nutrient solution usually takes place via 1 or 2 substance nozzles. Preferably, however, a liquid stream emerging from a bore in the nutrient solution inlet pipe is swirled via gas currents which emerge from neighbouring gas pipes and bring about a gas exchange in the system and break it into fine droplets. Bore size, pressure of liquid and gas and the geometry of the streams coming together can control the atomizing in wide limits.

In the simplest case of the device according to the invention, all elements, such as carrier plates, nutrient run in and run off devices and gas pipes are fixed centrally on the lid. In order to simplify the harvesting of the tissue or a culture exchange, it can, however, be advantageous to separate the lid part into an outer ring which carries the supply pipes and a middle lid part to which the carrier plate system is fixed. Thus, by means of lifting systems, the carrier plate system can be lifted out from the fermenter without loosening the connections of the supply pipes.

Preferably, in the case of such a dividing up, all pipes are attached to one side of the outer ring and passed on by ring tubes in the circumference of the outer ring. It is thereby made easier to engage from the other side into the opened reactor and to prevent a contamination during the engagement by passing over of a laminar, sterile air current.

The fermenters according to the invention usually have a volume of 10–250, preferably 50–100 l and are equipped with four cross-standing carrier plates.

A 100 l fermenter has, for example, a height of 85 cm in the case of a diameter of 28 cm and contains two plate crosses arranged over one another with 40 cm height and 20 cm breadth.

Insofar as horizontal or sloping plate systems are used, their distance is to be chosen as 5–25 cm, preferably about 10 cm. Thus, in the case of the present reactor, 4–10 plates are used.

In addition, this arrangement makes it possible to arrange two different cultures over one another, e.g. a root cell culture in the upper region and a leaf shoot culture in the lower region which can then possibly be additionally illuminated. Thus, more strongly formed intermediate products in the root cell region can be brought into the nutrient liquid on to the leaf culture where they are further reacted to the desired end products. By means of the vertical mounting of the carriers over one another, the nutrient medium drops off passively and makes unnecessary an additional transport expenditure as was previously usual when the different cultures were cultured in separate fermenters.

The nutrient solution is continuously circulated between fermenter and a nutrient solution tank. Interposed absorption columns in which the metabolites of the fermentation are absorbed on a suitable column material, filters for solid material floated out from the fermenter, inlets for nutrient material or devices for the removal of spent solution are provided as in case of known fermenters.

In an especially simple and economic embodiment the nutrient solution tank also consists of a simple plastic sack which, for reasons of stability, lies in a metal or synthetic material trough and is connected via a valve connection, for example luerlock closures, with the supply pipes. A magnetic stirrer device provides for a contamination-free mixing up of the sack content. In the case of the culture change, this economic tank can be disposed of directly and thus saves the usual laborious cleaning. By means of the arrangement in each case of one or more fermenters to a nutrient tank in a transportable stand, one obtains compact, mobile units.

In the following Figures, the invention is explained in more detail without, however, limiting it thereto.

Figure 1:
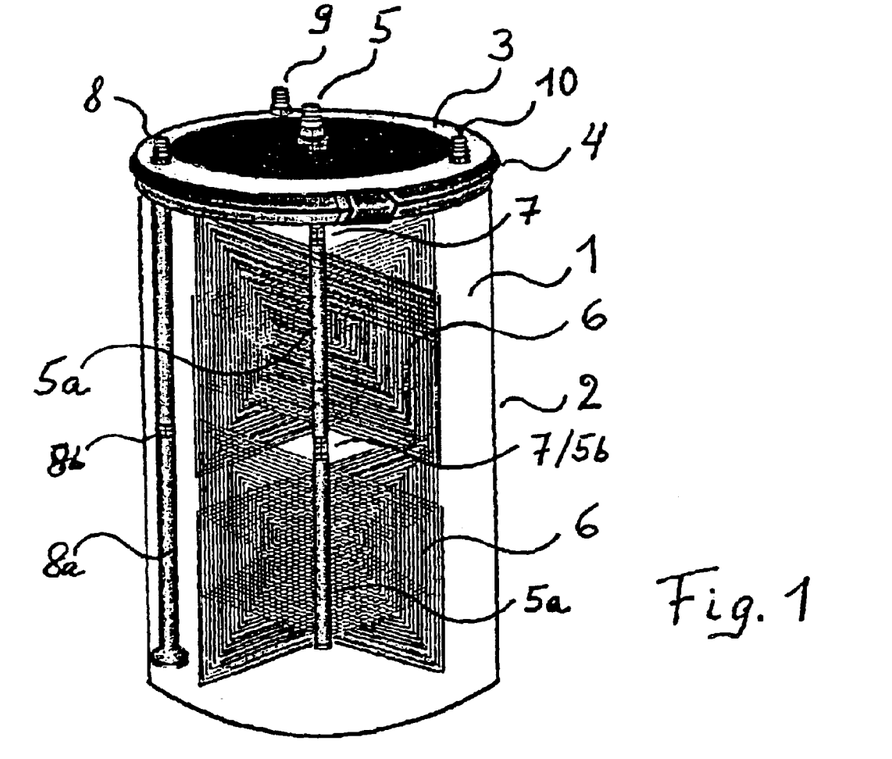
FIG. 1 shows a perspective view of a device according to the present invention.

FIG. 1 shows a fermenter 1 with external plastic tube 2 and lid part 3 which firmly holds the tube 2 via a squeeze closure 4. The lid 3 contains the central supply pipe 5 on which the carrier plates 6 are fixed in the form of a cross, in which the supply pipe 5 with the tube sections 5a and intermediate adapters 5b are integrated spray nozzles 7 for the nutrient solution. In the periphery of the lid 3 are provided a sucking-off pipe 8 for the spent nutrient solution and inlet and removal connections 9/10 for gases. In the illustrated case, two plate modules 6 are provided over one another.

Figure 2:
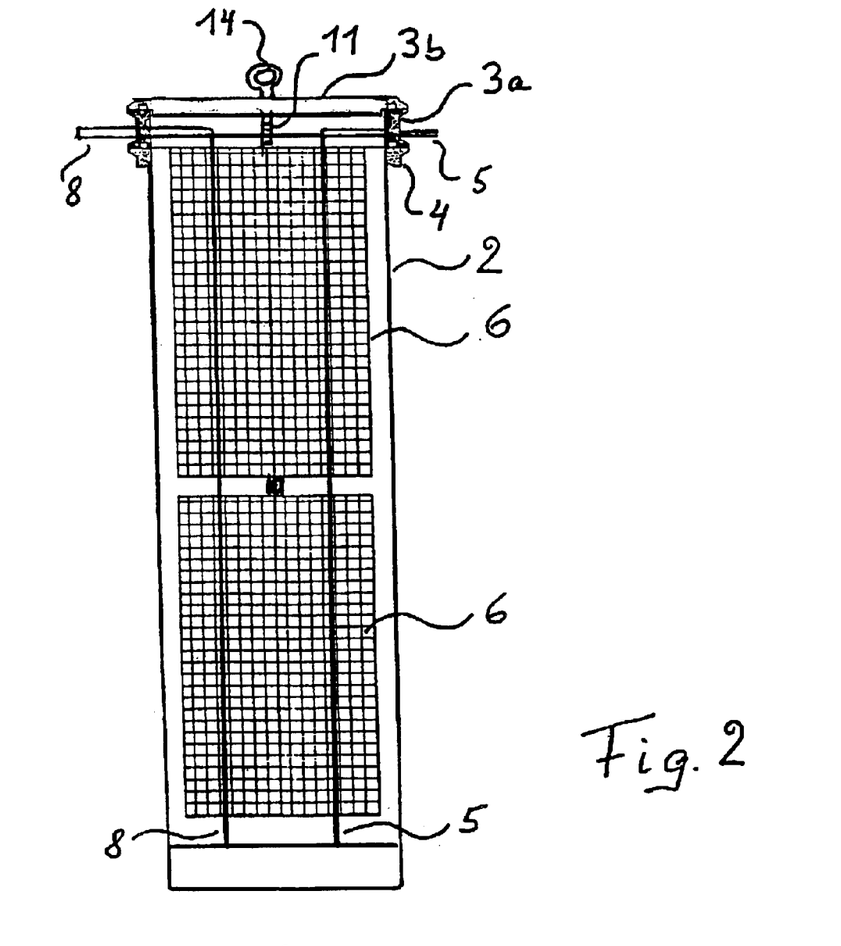
FIG. 2 shows a vertical cross sectional view of another device according to the present invention.

FIG. 2 shows a vertical section through another variant in which the supply and removal pipes 5, 8, 9, 10 are fixed in an outer ring 3a and run downwardly in the periphery of the fermenter 1. On the middle lid top 3b are fixed the carrier plates 6 via a central holding 11. The pipe 2 is firmly held between lid ring 3a and tension connection 4.

Figure 3:
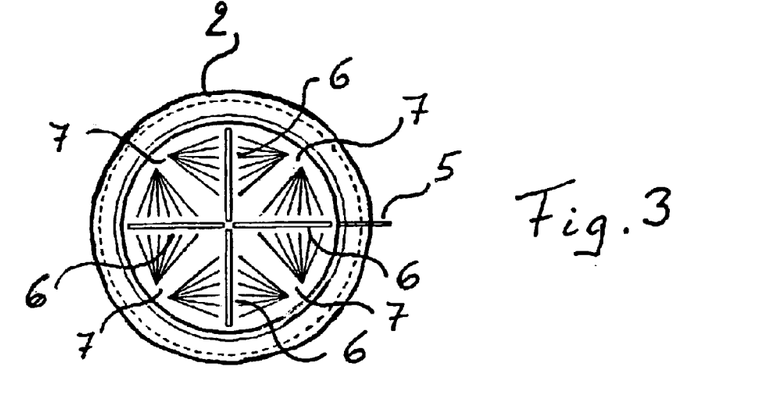
FIG. 3 shows a horizontal cross sectional view of the device in FIG. 2.

FIG. 3 shows the supplying of the nutrient solution in a horizontal sectional view according to FIG. 2 via the spray nozzles 7 which are assembled in the ring pipe 5c. Plastic tube 2 and carrier plates correspond to FIG. 2.

Figure 4:
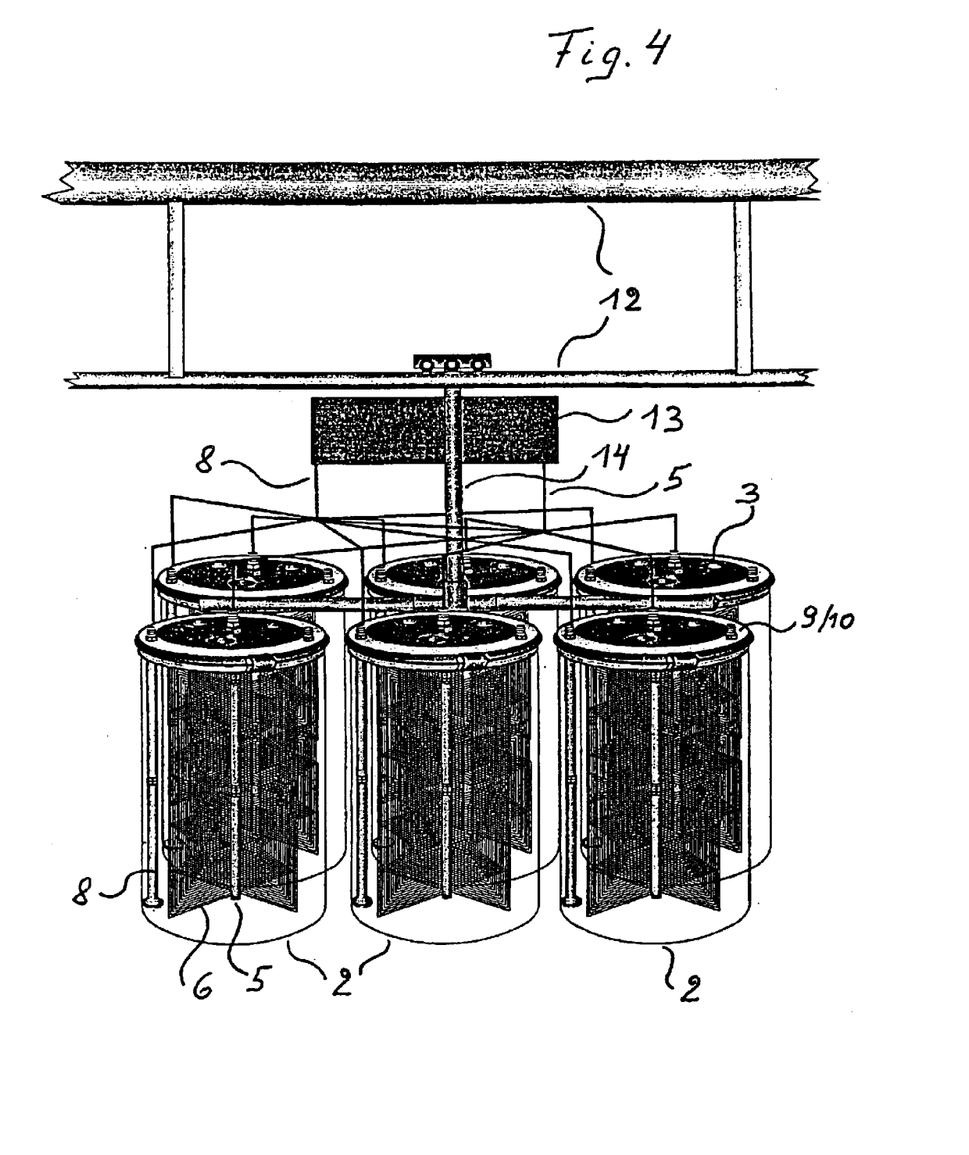
FIG. 4 shows six of the devices in FIG. 1 connected via appropriate pipe connections and holding devices to a central supply system (not shown).

FIG. 4 shows a group of fermenters 1 according to FIG. 1 which are transportably fixed via common holding device 14 to a rail system 12. Nutrient solution supply devices 5 and removal devices 8 are assembled and are connected via a not-shown pump device to the central nutrient solution tank 13.

Figure 5:
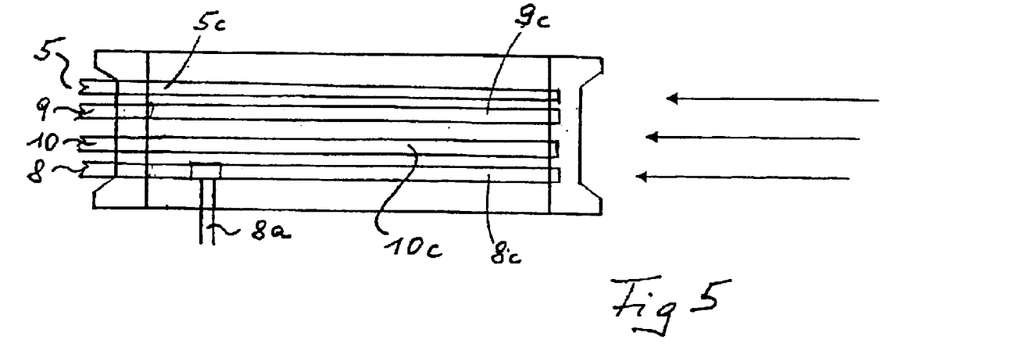
FIG. 5 shows an exploded view of the lid-part.

FIG. 5 shows a preferred construction of the lid ring 3a according to FIG. 2 in which all supply and removal pipes for liquids and gases 5, 8, 9 and 10 are mounted on one side and, via ring pipes 5c, 8c, 9c, 10c, a distribution over the circumference of the reactor takes place and from which go the passing over into the reactor. This construction has the advantage that, in the case of the opening of the reactor, sterile air can be blown in from the side facing away from the pipes which protects the reactor content from germ contamination (indicated by arrows on the right side). The ring pipes 5c, 8c, 9c, 10c preferably consist of a synthetic material tube which is guided in a recess or groove of the lid ring 3a and possesses T-shaped connection pieces for the pipes into the reactor. For reasons of illustration, only one connection 8a is shown.

Figures 6, 6A, 6B:
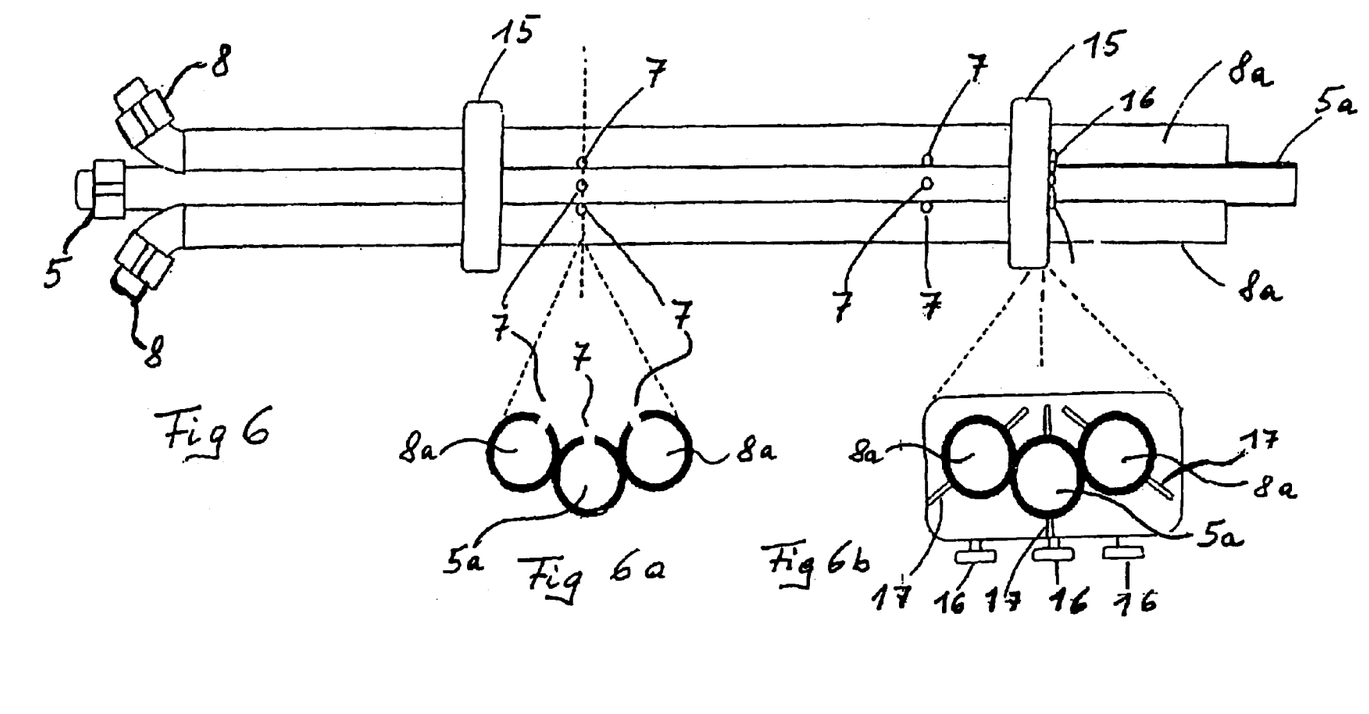
FIGS. 6, 6a, 6b show details of the supply and sucking off pipes according to an embodiment of the device according to the present invention.

FIG. 6 shows a preferred construction of the spray nozzles 7 for the nutrient solution in which gas supply pipes 8b are guided by holding means 15 parallel with the nutrient solution inlet 5b. At the height of the carrier plates 6, all three pipes 5a, 8a are provided with 0,1–1 mm sized bores 7 so that the nutrient solution stream emerging under pressure in operation from the middle pipe 5a is whirled by the gas stream emerging from the gas supply pipes 8a and divided up into fine droplets. Bore diameter and pressure, as well as the angle under which the gas streams impinge on the liquid, permit the spray character to be optimally adjusted.

FIG. 6a shows the arrangement of the spray nozzle bores 7.

FIG. 6b shows a holding means 15 for the pipes 5a, 8a, 8a, as well as adjustment devices 16, 17 with which the bores 7 can be aligned.

Figure 7:
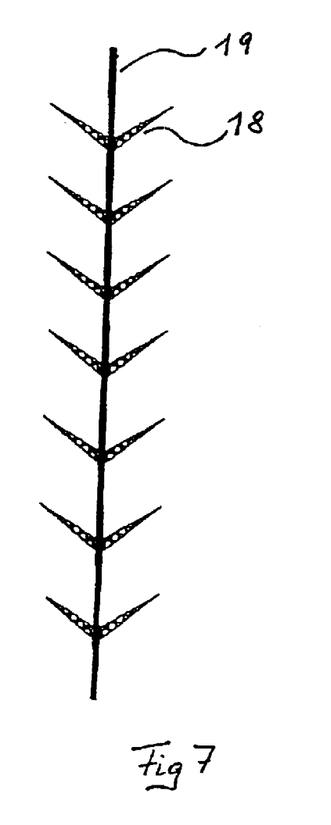
FIGS. 7, 7a, 7b show alternate embodiments of the carrier plates.

FIG. 7 shows a further construction of the carrier plate 6 in the form of preforated steel or aluminum sheets or synthetic resin plates which are attached on both sides to a central holding means 19 via not illustrated tilting hinges. The tilting hinges enable the tilting angle of the plates 18 (0–90°) and thus the run-off speed of the nutrient solution over the plates to be adjusted. Furthermore, it is possible to apply the plates 18 wholly on the holding means, whereby the device takes up less room, which, in the case of the cleaning and sterilizing of the device, requires smaller cleaning containers (cf. FIG. 7b).

Figure 7A:
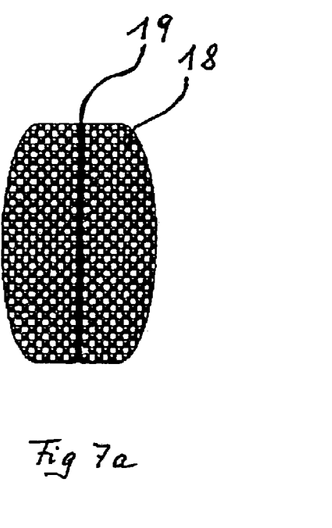
Figure 7B:
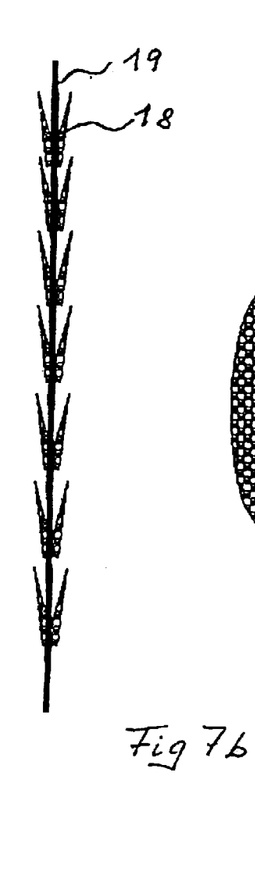

FIG. 7a shows schematically a perforated plate 18, as well as, in section, the central holding means 19 which is also preferably constructed as perforated plate or grid plate in order to make possible a gas and liquid passage. The plates 18 are arranged over one another at distances of 5–25 cm, preferably 10 cm, so that, depending upon the reactor height, there is given a number of 4–10.

List of References 1. fermenter vessel
2. plastic tube
3. lid
3a. outer lid ring
3b. middle ring cap
4. tension connections (squeeze connections)
5. supply pipe
5a. tube piece
5b. intermediate adapter
5c. ring pipes
6. carrier plates
7. spray nozzles
8. sucking-off pipe
8a. tube piece
8b. intermediate adapter
8c. ring pipe
9/10. gas inlet and outlet connections
9c/10c. ring pipe
11. central holding means
12. rail system
13. nutrient solution tank
14, 15. holding device
16, 17. adjustment device
18. perforated plates
19. central holding means

What is claimed is:

1. Device for the culturing of plant and animal tissue, comprising a fermenter vessel, an inlet for liquid nutrients and gases, as well as devices for removal of spent nutrient liquids and gases and solid carrier plates for the tissue which are permeable for the said liquid nutrients and the gases and are fixedly arranged within the fermenter vessel whereby the fermenter vessel comprises a form-stable lid part which carries the various inlet and outlet pipes as well as the carrier plates for the tissue and comprises a plastic tube, the opening of which is fixed against the lid and whereby the lid part and plastic tube are connected via seals and tension connections.

2. Device for the culturing of plant and animal tissue, comprising a fermenter vessel, an inlet for liquid nutrients and gases, as well as devices for removal of spent nutrient liquids and gases and solid carrier plates for the tissue which are permeable for the said liquid nutrients and gases and are fixedly arranged within the fermenter vessel whereby the fermenter vessel comprises a form-stable lid part which carries the various inlet and outlet pipes as well as the carrier plates for the tissue and comprises a plastic tube, the opening of which is fixed against the lid and whereby the lid part is connected via a screw and flange connection with a tension closure for the fixing of the plastic tube.

3. Device for the culturing of plant and animal tissue, comprising a fermenter vessel, an inlet for liquid nutrients and gases, as well as devices for removal of spent nutrient liquids and gases and solid carrier plates for the tissue which are permeable for the said liquid nutrients and gases and are fixedly arranged within the fermenter vessel whereby the fermenter vessel comprises a form-stable lid part which carries the various inlet and outlet pipes as well as the carrier plates for the tissue and comprises a plastic tube, the opening of which is fixed against the lid and whereby the lid part comprises an outer lid ring and a middle lid whereby the inlet for liquid nutrients and gases and the removal device for spent nutrient and gases are provided in the outer lid ring and the carrier plates are fixed on the middle lid via holding means and whereby the inlet and removal pipes are guided downwardly in the peripheral region of the fermenter vessel and a tension connection firmly holds the plastic tube against the outer lid ring.

4. Device according to claim 3, whereby all inlet and removal pipes are provided on one side of the lid ring and are guided over ring pipes in the lid ring over the circumference.

5. Device according to claim 3, whereby the carrier plates are arranged transversely to the longitudinal axis of the fermenter vessel.

6. Device according to claim 3, whereby the carrier plates are connected to a central holding means via tilt devices so that the carrier plates can be adjusted at an angle of 0–90° to the holding means.

7. Device for the culturing of plant and animal tissue, comprising a fermenter vessel, an inlet for liquid nutrients and gases, as well as devices for removal of spent nutrient liquids and gases and solid carrier plates for the tissue which are permeable for the said liquid nutrients and the gases and are fixedly arranged within the fermenter vessel whereby the fermenter vessel comprises a form-stable lid part which carries the various inlet and outlet pipes as well as the carrier plates for the tissue and comprises a plastic tube, the opening of which is fixed against the lid and whereby the supply pipes contain bores as nozzles for the outlet of nutrient solution and gas inlet pipes are provided and guided parallel to the supply pipes and also contain bores in appropriate places from which gas emerges.

8. Device for the culturing of plant and animal tissue, comprising a fermenter vessel, an inlet for liquid nutrients and gases, as well as devices for removal of spent nutrient liquids and gases and solid carrier plates for the tissue which are permeable for the said liquid nutrients and the gases and are fixedly arranged within the fermenter vessel whereby the fermenter vessel comprises a form-stable lid part which carries the various inlet and outlet pipes as well as the carrier plates for the tissue and comprises a plastic tube, the opening of which is fixed against the lid and whereby in the outer region of the fermenter vessel between the carrier plates are arranged one or more sucking-off pipes for spent nutrient liquid and spent gas which contain a sucking-off nozzle at the end.

9. Device for the culturing of plant and animal tissue, comprising a fermenter vessel, an inlet for liquid nutrients and gases, as well as devices for removal of spent nutrient liquids and gases and solid carrier plates for the tissue which are permeable for the said liquid nutrients and the gases and are fixedly arranged within the fermenter vessel whereby the fermenter vessel comprises a form-stable lid part which carries the various inlet and outlet pipes as well as the carrier plates for the tissue and comprises a plastic tube, the opening of which is fixed against the lid and whereby 3–8 plates are radially fixed on central holding means and the supply of the nutrient liquid takes place via 3–8 supply pipes present in the outer region between the carrier plates.

10. Device according to claim 9, whereby the carrier plates are arranged transversely to the longitudinal axis of the fermenter vessel.

11. Device according to claim 9, whereby the carrier plates are connected to a central holding means via tilt devices so that the carrier plates can be adjusted at an angle of 0–90° to the holding means.

12. Device for the culturing of plant and animal tissue, comprising a fermenter vessel, an inlet for liquid nutrients and gases, as well as devices for removal of spent nutrient liquids and gases and solid carrier plates for the tissue which are permeable for the said liquid nutrients and gases and are fixedly arranged within the fermenter vessel whereby the fermenter vessel comprises a form-stable lid part which carries the various inlet and outlet pipes as well as the carrier plates for the tissue and comprises a plastic tube, the opening of which is fixed against the lid and whereby the inlet pipe is a central pipe which comprises two or more tube pieces combined via intermediate adapters whereby the adapter contains nozzles for the atomisation of the nutrient solution and the tube pieces carry 3–8 radially projecting carrier plates for the cells whereby the length of the assembled supply pipe corresponds to the length of plastic tube of the fermenter vessel and the cross-section though the opening of the plastic tube or to the size of the lid.

13. Device according to claims 12, whereby in the outer region between the carrier plates one or more sucking off pipes for spent nutrient liquid and spent gases are arranged which also consist of tube pieces which correspond in length to the tube pieces of the supply pipe and contain adapter pieces for the connection of the tube pieces as well as a sucking-off nozzle on the end whereby the length of this pipe corresponds to the length of the plastic tube.

14. Device according to claim 12, whereby the nutrient liquid is circulated via a nutrient solution tank in the form of a plastic sack.

15. Device according to claim 3, whereby the plastic tube is formed of a thin synthetic resin foil.

16. Device according to claim 12, whereby the plastic tube is formed of a thin synthetic resin foil.

* * * * *